(12) United States Patent
Binder, Jr. et al.

(10) Patent No.: US 9,364,272 B2
(45) Date of Patent: Jun. 14, 2016

(54) BONE FIXATION PLATE

(75) Inventors: Lawrence J. Binder, Jr., Doylestown, PA (US); Matthew Hansell, Schwenksville, PA (US)

(73) Assignee: GLOBUS MEDICAL, INC., Audubon, PA (US)

(*) Notice: Subject to any disclaimer, the term of this patent is extended or adjusted under 35 U.S.C. 154(b) by 283 days.

(21) Appl. No.: 13/106,317

(22) Filed: May 12, 2011

(65) Prior Publication Data

US 2011/0213421 A1 Sep. 1, 2011

Related U.S. Application Data

(62) Division of application No. 10/826,285, filed on Apr. 19, 2004, now Pat. No. 7,963,981.

(51) Int. Cl.
*A61B 17/80* (2006.01)
*A61B 17/86* (2006.01)
(Continued)

(52) U.S. Cl.
CPC ......... *A61B 17/8033* (2013.01); *A61B 17/8038* (2013.01); *A61B 17/8042* (2013.01); *A61B 17/8047* (2013.01); *A61B 17/8052* (2013.01); *A61B 17/844* (2013.01); *A61B 17/861* (2013.01); *A61B 17/1728* (2013.01); *A61B 2017/8655* (2013.01)

(58) Field of Classification Search
CPC ............... A61B 17/86; A61B 17/8033; A61B 17/8038; A61B 17/8042; A61B 17/8047; A61B 17/8052; A61B 17/84; A61B 17/844

USPC ............ 606/300, 301, 304–308, 70, 71, 280, 606/286–296
See application file for complete search history.

(56) References Cited

U.S. PATENT DOCUMENTS 4,484,570 A 11/1984 Sutter et al.
5,135,210 A 8/1992 Michelson
(Continued)

FOREIGN PATENT DOCUMENTS

| EP | 0809975 A2 | 12/1997 | |
| WO | WO 8803781 A1 * | 6/1988 | ............... A61F 2/44 |
| WO | 9722306 A1 | 6/1997 | |

OTHER PUBLICATIONS

Machine Translation of WO 88/03781 retrieved from the EPO website <http://translationportal.epo.org/emtp/translate/?ACTION=description-retrieval&COUNTRY=WO&ENGINE=google&FORMAT=docdb&KIND=A1&LOCALE=en_EP&NUMBER=8803781&OPS=ops.epo.org/3.1&SRCLANG=de&TRGLANG=en> on Aug. 13, 2015.*

(Continued)

*Primary Examiner* — Larry E Waggle, Jr.

(57) ABSTRACT

An apparatus for reducing the profile of a bone fixation plate while, preventing backing out of screws is disclosed. The apparatus includes at least one section of relief and sections of engagement. The plate has at least two openings though which two screws can pass through bony tissue. As the screw is tightened, it will begin to lag the plate to the bone. When the screw head interferes with the plate at the interference point, there is a slight resistance that insertion forces can overcome. When the screw is advanced further, it snaps into the sliding fit area and is allowed to move freely. The forces that cause the screw to back out from the plate are preferably not strong enough to pass the screw head back past the interference section. It may be desirable to include a set screw to help prevent backout.

15 Claims, 10 Drawing Sheets

(51) Int. Cl.
*A61B 17/84* (2006.01)
*A61B 17/17* (2006.01)

(56) References Cited

U.S. PATENT DOCUMENTS

| | | | |
|---|---|---|---|
| 5,151,103 A | 9/1992 | Tepic et al. | |
| 5,250,061 A | 10/1993 | Michelson | |
| 5,364,399 A | 11/1994 | Lowery et al. | |
| 5,484,437 A | 1/1996 | Michelson | |
| 5,505,732 A | 4/1996 | Michelson | |
| 5,513,827 A | 5/1996 | Michelson | |
| 5,522,899 A | 6/1996 | Michelson | |
| 5,549,612 A | 8/1996 | Yapp et al. | |
| 5,578,034 A | 11/1996 | Estes | |
| 5,626,266 A | 5/1997 | Michelson | |
| 5,653,713 A | 8/1997 | Michelson | |
| 5,662,300 A | 9/1997 | Michelson | |
| 5,735,853 A | 4/1998 | Olerud | |
| 5,776,199 A | 7/1998 | Michelson | |
| 5,797,909 A | 8/1998 | Michelson | |
| 6,032,309 A | 3/2000 | Michelson | |
| 6,039,740 A * | 3/2000 | Olerud | 606/309 |
| 6,080,155 A | 6/2000 | Michelson | |
| 6,083,228 A | 7/2000 | Michelson | |
| 6,096,038 A | 8/2000 | Michelson | |
| 6,117,173 A | 9/2000 | Taddia et al. | |
| 6,120,503 A | 9/2000 | Michelson | |
| 6,136,001 A | 10/2000 | Michelson | |
| 6,139,550 A | 10/2000 | Michelson | |
| 6,142,997 A | 11/2000 | Michelson | |
| 6,152,927 A | 11/2000 | Farris et al. | |
| 6,159,214 A | 12/2000 | Michelson | |
| 6,190,388 B1 | 2/2001 | Michelson et al. | |
| 6,193,721 B1 | 2/2001 | Michelson | |
| 6,200,320 B1 | 3/2001 | Michelson | |
| 6,210,412 B1 | 4/2001 | Michelson | |
| 6,235,033 B1 | 5/2001 | Brace et al. | |
| 6,241,731 B1 * | 6/2001 | Fiz | 606/65 |
| 6,241,770 B1 | 6/2001 | Michelson | |
| 6,257,459 B1 | 7/2001 | Michelson | |
| 6,269,974 B1 | 8/2001 | Michelson | |
| 6,270,498 B1 | 8/2001 | Michelson | |
| 6,283,969 B1 * | 9/2001 | Grusin et al. | 606/280 |
| 6,299,030 B1 | 10/2001 | Michelson | |
| 6,306,139 B1 | 10/2001 | Fuentes | |
| 6,318,602 B1 | 11/2001 | Michelson | |
| 6,350,283 B1 | 2/2002 | Michelson | |
| 6,364,880 B1 | 4/2002 | Michelson | |
| 6,383,186 B1 | 5/2002 | Michelson | |
| 6,398,783 B1 | 6/2002 | Michelson | |
| 6,413,259 B1 | 7/2002 | Lyons et al. | |
| 6,416,528 B1 | 7/2002 | Michelson | |
| 6,428,542 B1 | 8/2002 | Michelson | |
| 6,436,098 B1 | 8/2002 | Michelson | |
| 6,440,139 B2 | 8/2002 | Michelson | |
| 6,447,547 B1 | 9/2002 | Michelson | |
| 6,454,769 B2 | 9/2002 | Wagner et al. | |
| 6,454,771 B1 | 9/2002 | Michelson | |
| 6,478,823 B1 | 11/2002 | Michelson | |
| 6,500,205 B1 | 12/2002 | Michelson | |
| 6,503,250 B2 | 1/2003 | Paul | |
| 6,517,544 B1 | 2/2003 | Michelson | |
| 6,527,776 B1 | 3/2003 | Michelson | |
| 6,537,279 B1 | 3/2003 | Michelson | |
| 6,537,320 B1 | 3/2003 | Michelson | |
| 6,561,388 B2 | 5/2003 | Michelson et al. | |
| 6,565,566 B1 * | 5/2003 | Wagner et al. | 606/267 |
| 6,575,977 B1 | 6/2003 | Michelson | |
| 6,592,586 B1 | 7/2003 | Michelson | |
| 6,602,256 B1 | 8/2003 | Hayes | |
| 6,605,090 B1 | 8/2003 | Trieu et al. | |
| 6,616,666 B1 | 9/2003 | Michelson | |
| 6,620,163 B1 | 9/2003 | Michelson | |
| 6,652,525 B1 | 11/2003 | Assaker et al. | |
| 6,652,584 B2 | 11/2003 | Michelson | |
| 6,666,890 B2 | 12/2003 | Michelson | |
| 6,679,883 B2 | 1/2004 | Hawkes et al. | |
| 6,692,501 B2 | 2/2004 | Michelson | |
| 6,692,503 B2 | 2/2004 | Foley et al. | |
| 6,695,846 B2 | 2/2004 | Richelsoph et al. | |
| 6,695,849 B2 | 2/2004 | Michelson | |
| 6,709,458 B2 | 3/2004 | Michelson | |
| 6,712,818 B1 | 3/2004 | Michelson | |
| 6,716,247 B2 | 4/2004 | Michelson | |
| 6,730,093 B2 | 5/2004 | Saint Martin | |
| 6,730,127 B2 | 5/2004 | Michelson | |
| 6,733,535 B2 | 5/2004 | Michelson | |
| 6,749,636 B2 | 6/2004 | Michelson | |
| 6,755,833 B1 | 6/2004 | Paul | |
| 6,770,074 B2 | 8/2004 | Michelson | |
| 6,793,679 B2 | 9/2004 | Michelson | |
| 6,808,537 B2 | 10/2004 | Michelson | |
| 6,814,756 B1 | 11/2004 | Michelson | |
| 6,875,213 B2 | 4/2005 | Michelson | |
| 6,890,355 B2 | 5/2005 | Michelson | |
| 6,890,358 B2 | 5/2005 | Ball et al. | |
| 6,896,676 B2 | 5/2005 | Zubok et al. | |
| 6,896,680 B2 | 5/2005 | Michelson | |
| 6,916,320 B2 | 7/2005 | Michelson | |
| 6,926,718 B1 | 8/2005 | Michelson | |
| 6,936,050 B2 | 8/2005 | Michelson | |
| 6,936,051 B2 | 8/2005 | Michelson | |
| 6,945,973 B2 | 9/2005 | Bray | |
| 6,962,606 B2 | 11/2005 | Michelson | |
| 6,966,912 B2 | 11/2005 | Michelson | |
| 6,969,390 B2 | 11/2005 | Michelson | |
| 6,972,019 B2 | 12/2005 | Michelson | |
| 6,972,035 B2 | 12/2005 | Michelson | |
| 6,986,772 B2 | 1/2006 | Michelson | |
| 7,008,453 B1 | 3/2006 | Michelson | |
| 7,011,663 B2 | 3/2006 | Michelson | |
| 7,022,137 B2 | 4/2006 | Michelson | |
| 7,255,699 B2 | 8/2007 | Paul | |
| 7,311,712 B2 * | 12/2007 | Dalton | 606/71 |
| 7,846,190 B2 * | 12/2010 | Ball | 606/313 |
| 2002/0016595 A1 * | 2/2002 | Michelson | 606/73 |
| 2002/0065517 A1 | 5/2002 | Paul | |
| 2002/0133158 A1 | 9/2002 | Saint Martin | |
| 2002/0143328 A1 | 10/2002 | Shluzas et al. | |
| 2002/0147450 A1 | 10/2002 | LeHuec et al. | |
| 2003/0073996 A1 * | 4/2003 | Doubler et al. | 606/61 |
| 2003/0093078 A1 * | 5/2003 | Ritland | 606/73 |
| 2003/0100904 A1 * | 5/2003 | Biedermann | 606/73 |
| 2003/0149434 A1 | 8/2003 | Paul | |
| 2003/0187440 A1 | 10/2003 | Richelsoph et al. | |
| 2003/0220642 A1 * | 11/2003 | Freudiger | 606/61 |
| 2004/0030338 A1 | 2/2004 | Paul | |
| 2004/0073218 A1 | 4/2004 | Dahners | |
| 2004/0097940 A1 | 5/2004 | Paul | |
| 2004/0133205 A1 | 7/2004 | Thramann et al. | |
| 2005/0033294 A1 | 2/2005 | Garden et al. | |
| 2005/0071013 A1 | 3/2005 | Zubok et al. | |
| 2005/0085812 A1 | 4/2005 | Sherman et al. | |
| 2005/0149026 A1 | 7/2005 | Butler et al. | |
| 2005/0165400 A1 | 7/2005 | Fernandez | |
| 2005/0234455 A1 | 10/2005 | Binder et al. | |
| 2005/0261681 A9 | 11/2005 | Branch et al. | |
| 2005/0261690 A1 | 11/2005 | Binder et al. | |

OTHER PUBLICATIONS

Regis W. Haid, MD et al., "The Cervical Spine Study Group anterior cervical plate nomenclature", Neurosurg Focus, vol. 12, Jan. 2002.

* cited by examiner

BONE FIXATION PLATE

CROSS REFERENCE TO RELATED APPLICATIONS

This patent application is a divisional application claiming priority to U.S. patent application Ser. No. 10/826,285 filed on Apr. 19, 2004 now U.S. Pat. No. 7,963,981, the entire contents of which are incorporated by reference.

FIELD OF THE INVENTION

The present invention relates to a bone fixation plate used to stabilize vertebrae and other bony anatomy. More specifically, the present invention relates to a cervical plate having a minimized profile that easily and reliably prevents backout of fastening devices.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

The cervical spine has presented the most challenges for doctors, partially due to the small size of the vertebrae and the spacing between adjacent vertebrae. Typically, weaknesses in the cervical spine are corrected by using devices that fuse one or more vertebrae together. Common devices involve plate systems that align and maintain adjacent cervical vertebrae in a desired position, with a desired spacing.

These devices commonly referred to as bone fixation plating systems, typically include one or more plates and screws for aligning and holding vertebrae in a fixed position with respect to one another. Initial devices used stainless steel plates and screws. In order to remain fixed in place, the screws were required to pass completely through the vertebrae and into the spinal canal. These devices caused many complications and involved significant risks. To allow a screw to pass, drilling and then tapping of the vertebrae was required. In the process, instruments came within close proximity of the spinal cord, which required extreme care on the part of the surgeon.

In addition to the risks of surgically applying bone fixation plates, other complications arose. Commonly, these problems involve loosening and failure of the hardware. Two common failures are the breakage of the plates, and the backing out of the screws into soft tissues of the patient's body. The backing out of the screws is typically a result of the screws failure to achieve a sufficient purchase in the bone, although the stripping of the screws has also been known to cause this problem. Regardless of the cause of the hardware failures, a surgeon must repair or replace the broken parts, which requires undesirable invasive procedures.

Advances in material science allowed engineers to manufacture bone fixation plates out of materials that would resist breakdown within a body. However, the backing out of screws remained a problem. Many solutions were devised in an attempt to prevent this from occurring. One prevalent solution involved minimizing the length of the screw in order to prevent screw to plate junction breakage of the screw. However, the shortened screw is typically unable to achieve a sufficient purchase in the bone. Shortened screws often provide very little holding power and inadequate tactile feedback to the surgeon. Tactile feedback to the surgeon is important to signal completion of tightening prior to stripping of the screw within the bone.

An alternate solution involves increasing the length of the screws in order to achieve sufficient purchase to hold the plate in place. While the use of longer screws can provide bicortical fixation, this method also has its drawbacks. Primarily, long screws increase the chances of interference with each other when they are screwed into bony tissue at an angle. In addition, many bone fixation plating systems place bone grafts between vertebrae. The bone grafts are eventually supposed to spur the growth of bone between the vertebrae, so that the vertebrae become fused together naturally.

In order for this to occur, the bone fixation plating needs to maintain a desired spacing between the vertebrae, which is filled by the bone grafts. However, it is common for the bone grafts to experience compression, which separates at least one of the adjacent vertebrae from the bone graft. Cervical plates that employ long screws do not allow for sufficient movement of the vertebrae to accommodate the compression of the bone graft, because the purchase of the screws is too great. Thus, the vertebrae cannot move and are unable to adjusting to the compression of the bone graft.

Another method of preventing the backing out of screws involves placing a second plate over the screws. This second plate functions to interlock the screws, preventing them from backing out. However, this method of securing screws often becomes bulky, resulting in a large and undesirable profile. In addition, these configurations require carrying out multiple steps or using a multi-piece assembly in order to block an opening through which a loose fastener head may pass. For instance, the use of a c-ring that can expand as the fastener head is inserted requires additional components and assembly time to form a plate. Moreover, multi-component designs may lose their ability to retain a fastener over time due to material failure, relaxation, or the like. Additionally, multi-component configurations may not provide sufficient ability to lag the plate to the vertebral body.

One additional drawback of many designs is that they add to the overall height of the plate. It is desirable to maintain a low profile design for many reasons, such as to minimize irritation to surrounding tissue. For example a plate design having a high overall height or a receptacle design that does not prevent screw backout may cause a patient to suffer from dysphasia. Ultimately, the screw or plate may irritate or wear through neighboring tissue. In addition, a high height plate or unretained loose screw in the lumbar spine may be abrasive to the aorta or vena cava. Severe abrasion by the plate or screw in this instance may puncture the aorta or vena cava and cause internal bleeding.

In addition, many of these plates were not designed to allow for the locking of all of the screws, which left some of the screws susceptible to backout caused by tiny vibrations, or micromotion. Some methods attempted to reduce the profile of the total system by using small parts. However, this led to the small parts falling off and getting lost. In addition, the smaller parts are fragile and require special instruments in order to insert or manipulate them. In addition, because of their small size, incorrect placement relative to the axis of the plate often causes sharp and jagged shavings to be formed as a locking screw contacts an improperly seated bone screw.

Prior attempts at increasing the screw purchase have resulted in risky procedures, or an insufficient ability to adapt to movement. Attempts and decreasing the profile of bone fixation plates have resulted in lost parts, or insufficient purchase. A continuing need exists for an apparatus that is able to quickly and reliably lock a plurality of screws into place while maintaining a low profile.

SUMMARY OF THE INVENTION

The present invention relates to an apparatus for connecting a plate to a bone. This may be desirable in order to immobilize, for example, two cervical vertebrae. In one embodiment, the present invention comprises at least one screw and a plate having at least one opening. As the screw passes through the opening and is tightened, it begins to lag the plate to the bone. When the screw head interferes with the plate at an interference point, there is a slight resistance force that insertion forces can easily overcome. When the screw is advanced further, it snaps into the sliding fit area and is allowed to move freely. Forces which can cause the screw to back out of from the plate are preferably not strong enough to pass the screw head past the interference section. In some embodiments, it may be desirable to use a set screw to aid in preventing backout. Alternately, a clamp applied to the head of the screw to prevent rotation may be desired.

In one embodiment, the present invention comprises an apparatus for fixing a plate to bony material, comprising at least one opening having a spherical curvature. Also included is at least one fastener having a head that interferes with the spherical curvature at an interference point. In this embodiment, the head is capable of engaging with and passing the interference point to communicate with the spherical curvature.

In some embodiments, the spherical curvature includes at least one engagement area and at least one relief area. The tangents to the spherical curvature preferably intersect to form an angle. Preferably, the angle of intersection of the tangents is between about 1 and about 5 degrees. More preferably, the angle of intersection of the tangents is between about 1 and about 3 degrees.

It is desirable to limit the relief areas in some embodiments to prevent a screw from passing through the interference point. Accordingly, it is preferred that the relief area comprises less than about 40% of the circumference of the spherical curvature. More preferably, the relief area comprises less than about 30% of the circumference of the spherical curvature. In some embodiments, it may be desirable to provide an additional opening that is configured and dimensioned to increase the magnitude of interference at the interference point.

In another embodiment, the present invention comprises an apparatus for stabilizing at least two bony structures, comprising a plate where more than one aperture is configured and adapted to include an interference area. The interference area is integrally formed in the plate to prevent a fastener from backing out of the interference area.

In this embodiment, a fastener, such as a screw, is capable of engaging with and passing through the interference area. The interference area is part of spherical curvature, which has at least one engagement area and at least one relief area.

Preferably, the tangents to the spherical curvature intersect. It is desirable to have the angle of intersection of the tangents between about 1 and 5 degrees. In some embodiments, it is also preferable to include another opening that is selectively positioned to increase the magnitude of interference at the interference point. The opening may be configured and adapted such that it is able to pass a wedge shaped screw.

In another embodiment, the present invention comprises an apparatus for fixing a plate to bony material consisting essentially of at least one opening having a spherical curvature. At least one fastener having a head capable of engaging with and passing through an interference point of the spherical curvature is also included. In this embodiment, the fastener is prevented from backing out of the opening by the interference point. In this embodiment, the tangents to the spherical curvature intersect. As described above, another opening may be selectively positioned to increase the magnitude of interference at the interference point.

DETAILED DESCRIPTION OF THE PREFERRED EMBODIMENTS

The present invention relates to a bone fixation plate that minimizes the problems associated with prior bone fixation plates while maintaining a small profile. In one embodiment, as a screw is tightened, it will begin to lag the plate to the bone. When the screw head interferes with the plate at an interference point, a slight resistance is generated. The insertion forces can easily overcome this resistance. When the screw is advanced further, it snaps into a sliding fit area and is allowed to move freely. The forces which can cause the screw to back out from the plate are preferably not strong enough to pass the screw head back past the interference section. It may be desirable to include a set screw to prevent backout of the screws due to micromotion. In other embodiments, the head of the screw may be clamped to prevent rotation, when such a restriction on the movement of the screw is desirable.

The present invention provides a locking mechanism that allows one or more bone screws used for attaching a plate to vertebrae to be easily and reliably locked in place at the same time by a single operation. When fully installed, the locking mechanism has a low profile and maintains its ability to prevent breakout of screws due to micromotion. The present invention may be used on the anterior or posterior of the vertebrae. Although the present invention is described with respect to two bone fixation vertebrae, it will be understood that the following embodiments are capable of being used with any number of vertebra, in any spinal location.

Figure 1:
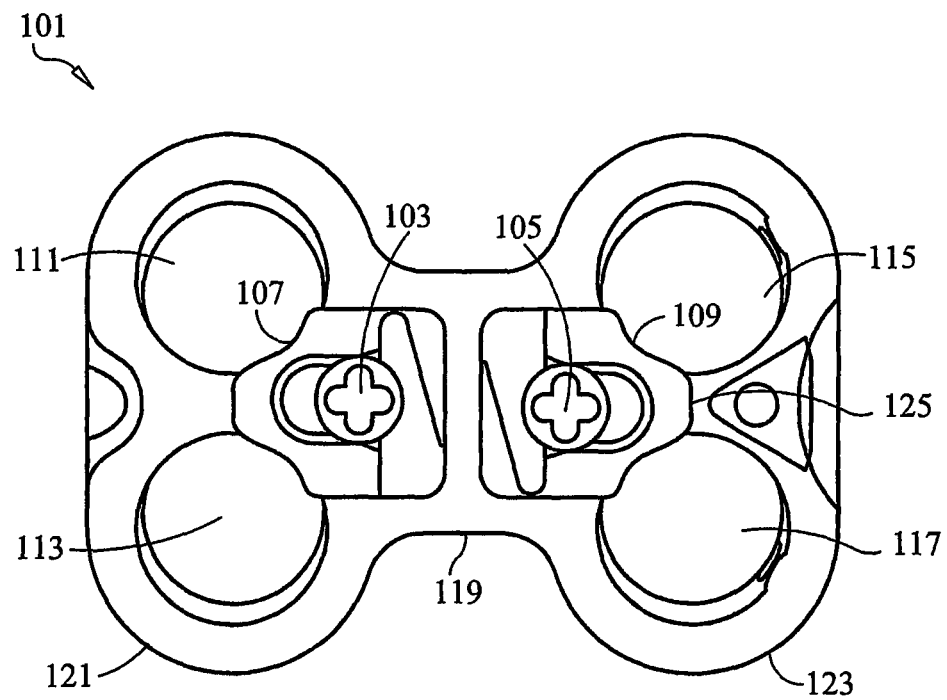
FIG. 1 is a diagram showing one embodiment of the bone fixation plate according to the present invention.

Turning now to the drawings, FIG. 1 shows one embodiment of a bone fixation plate 101 according to the present invention. The plate may be secured to two vertebrae in order to maintain the vertebrae integrally with respect to one another in a desired orientation and at a desired spacing from one another. Plate 101 includes two fastening devices, such as screws 103-105 or the like, which are operatively communicable with spring loaded plates 107-109. The plate also includes four openings 111-117, through which screws (not shown) may be used to fasten the plate 101 to the vertebrae.

The plate 101 and the screws may be comprised of any material, such as a metal, alloy, or any combination of the two. Preferably, the material used to construct the plate and the screws allows the plate 101 to maintain its structural integrity while allowing for a desired amount of resiliency. Furthermore, the material used is preferably bio-compatible and capable of withstanding the conditions of a body over a desired period of time. In some embodiments, this is achieved by manufacturing the plate 101 and screws using metals such as titanium or stainless steel. Titanium has sufficient ductility to permit a desired amount of curving of the plate 101 to conform to the shape of the vertebrae, yet has the strength to maintain its structural integrity.

In the FIG. 1 embodiment, the bone fixation plate 101 comprises a center portion 119 and two distal portions 121-123. Each distal portion 121-123 may be attached to a different vertebra using fasteners, such as screws, that pass through openings 111-117. Because distal portions 121-123 are similar, only the operation of distal portion 121 is described in detail.

Figure 2:
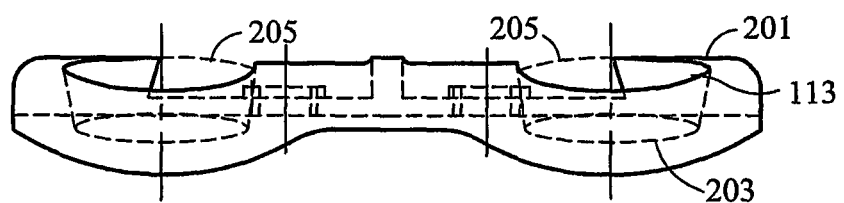
FIG. 2 is a diagram showing a side view of exemplary openings according to the present invention.

FIG. 2 is a diagram showing a side view of openings 111 and 113. In one embodiment, each opening has a substantially circular shape, as shown in FIG. 1. In this embodiment, the inner portion of openings 111-113 have substantially spherical curvatures. Accordingly, the radius of the inner portion of openings 111-113 decrease in diameter from the top 201 of the openings, to the bottom 203 of the openings. Preferably, the spherical curvature of the openings 111-113 may accommodate a screw having a spherical head. However, the present invention is not limited to spherical curvatures or spherical heads. In other embodiments, any complementary head and receptacle may be used. Preferably, the complementary head and receptacle are capable of preventing the breakout of the screw.

As shown in FIG. 2, the openings 111-113 are not continuous. It is desirable that the openings 111-113 comprise only a portion of the circumference of the spherical curvature. In one embodiment, the remaining portion 205 of the circumference of the spherical curvature of the openings 111-113 is provided by spring loaded plate 107, shown in FIG. 1. The portion of the circumference of the spherical curvature that is completed by spring loaded plate 107 may be varied as desired, for example, according to the amount of resistance that is desired by the spring loaded plate 107. In one embodiment, the openings 111-113 comprise at least 60 percent or more of the total circumference of the spherical curvature. In another embodiment, the openings 111-113 comprise at least 70 percent or more of the total circumference of the spherical curvature. In yet another embodiment, the openings 111-113 comprise at least 80 percent or more of the total circumference of the spherical curvature.

Figure 3A:
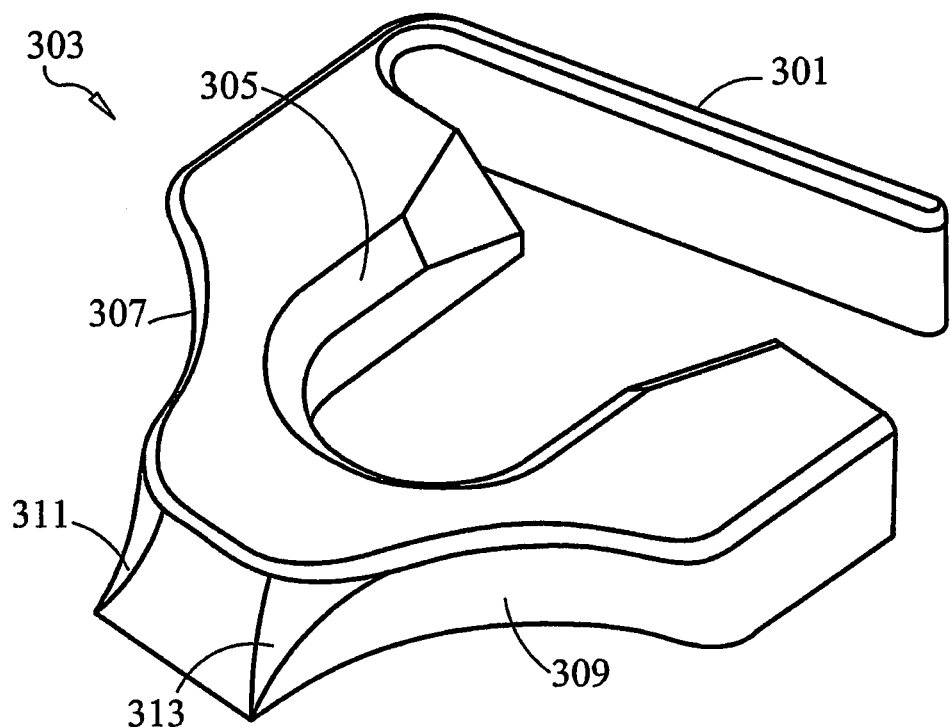
FIG. 3A is a diagram showing one embodiment of the spring loaded plate according to the present invention.

FIG. 3A is a diagram showing one embodiment of the spring loaded plate 107. In this embodiment, the spring loaded plate 107 includes arm 301. When a force causes arm 301 to be deflected towards the body 303 of the spring loaded plate 107, potential energy is stored in the arm 301. This potential energy causes the arm 301 to generate spring-like forces that have a tendency to force it away from the body 303, and back to its natural resting position shown in FIG. 3A. When the deflection force is removed, the potential energy is converted to kinetic energy, and forces the body 303 away from the arm 301. In other embodiments, the spring loaded plate 107 does not have to have a free cantilever load such as the arm 301 shown in FIG. 3A. For example, it may be desirable to use a loop, or the like, to resist movement of the spring loaded plate 107.

Figure 3B:
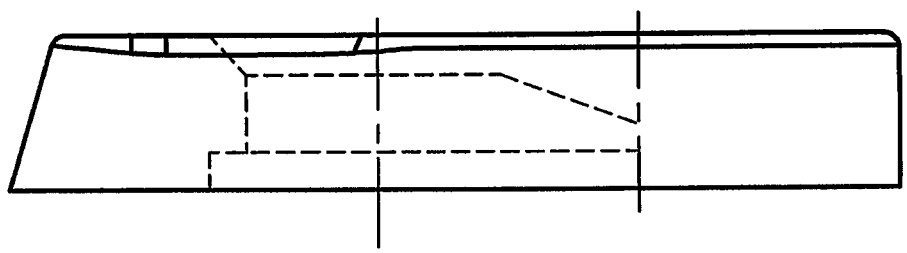
FIG. 3B is a diagram showing an exemplary ramped surface included in the spring loaded plate of FIG. 3A.

The inner portion of plate 107 preferably comprises a ramped surface 305. In one embodiment, the ramped surface 305 is selectively engageable with screw 103, shown in FIG. 1. When the screw 103, is engaged by the ramped surface shown in FIG. 3B, outward forces are generated on the screw, preventing it from backing out. As the angle of the ramped surface increases, the forces that are exerted on the screw 103 increase. Thus, the angle of the ramped surface may be chosen based on the amount of force that is desired to keep the screw 103 from backing out.

In one embodiment, the angle of the ramp is between about 5 and 50 degrees. In another embodiment, the angle of the ramp is between about 10 and about 30 degrees. In yet another embodiment, the angle of the ramp is between about 15 and 25 degrees.

The spring loaded plate 107 comprises two spherical curvatures 307 and 309. Spherical curvatures 307 and 309 complete the spherical curvatures of openings 111 and 113. Each curvature 307-309 comprises a spherical curvature having a radius that decreases from top to bottom, as discussed with respect to the curvatures of openings 111 and 113. The spherical curvatures 307-309 may comprise any desired percentage of the circumference of the total spherical curvature. In one embodiment, each curvature 307-309 may comprise 20 percent or less of the total circumference of the spherical curvature. In another embodiment, each curvature 307-309 may comprise 30 percent or less of the total circumference of the spherical curvature. In yet another embodiment, each curvature 307-309 may comprise 40 percent or less of the total circumference of the spherical curvature.

Spring loaded plate 107 also includes two edges 311 and 313, shown in FIG. 3A. Each edge is preferably configured and dimensioned to be engageable with a depression 125 in plate 101. In one embodiment, the spring loaded plate 107 is positioned within the depression 125. Depression 125 is configured and dimensioned such that there is sufficient space for plate 107 to move between its compressed and relaxed states, described with respect to FIGS. 3A and 3B. In one embodiment, plate 107 is prevented from horizontally exiting depression 125 by the protrusion formed by openings 111-113.

Figure 4A:
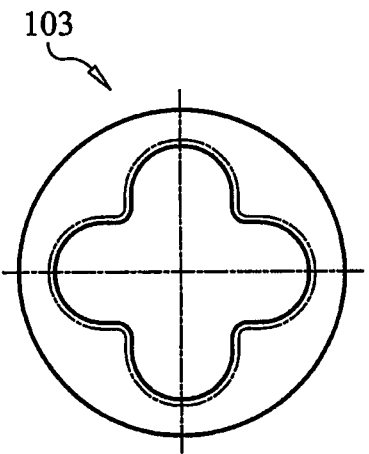
FIGS. 4A and 4B are diagrams showing an exemplary embodiment of a set screw according to the present invention.
Figure 4B:
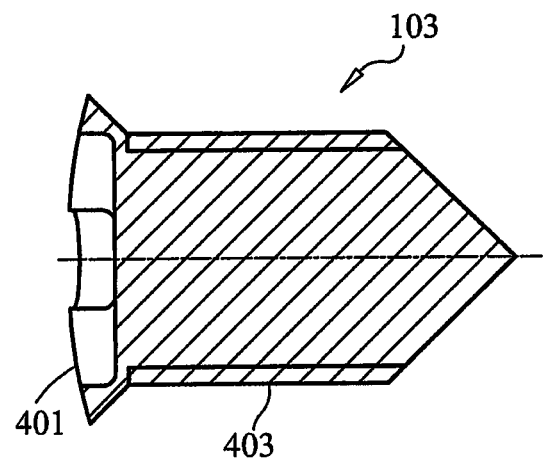

In one embodiment, shown in FIGS. 4A and 4B, the screw 103 may have an angled head 401. It may be desirable for screw 103 to have threads along its elongate shaft 403. In order to aid in tightening screw 103, it preferably includes a projection with a curved surface to aid in gripping the screw. The length of the elongate shaft may be varied as desired. In one embodiment, the length of the elongate shaft is about 5 mm or less. In another embodiment, the length of the elongate shaft is about 3 mm or less. In yet another embodiment, the length of the elongate shaft is about 1 mm or less.

Figure 5A:
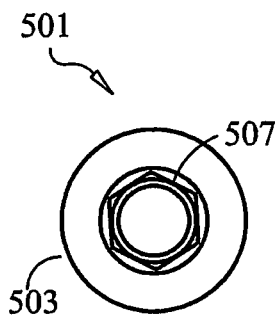
FIGS. 5A and 5B are diagrams showing an exemplary embodiment of a bone screw according to the present invention.
Figure 5B:
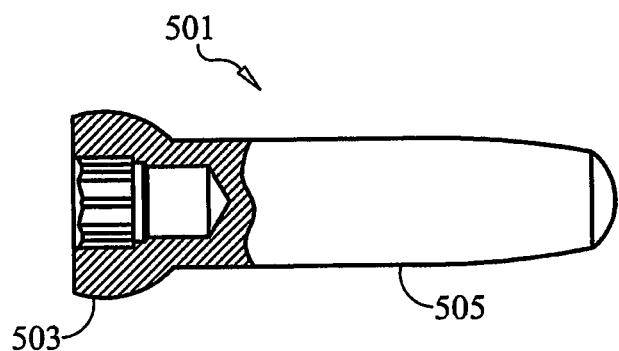

FIGS. 5A and 5B are diagrams showing one embodiment of the screw that is used to connect plate 101 to vertebrae. Screw 501 preferably has a spherical head 503 that is selectively engageable with the spherical curvature. An elongate shaft 505 is connected to the spherical head 503 to allow it to penetrate bony tissue of the vertebrae. Preferably, the elongate shaft 505 includes threads that aid in fixing the plate 101 to a vertebra. As shown in FIG. 5B, it is desirable to have a hexagonal projection 507 to aid in gripping the screw.

The length of the elongate shaft 505 may be varied as desired. In one embodiment, the length of the elongate shaft is about 20 mm or less. In another embodiment, the length of the elongate shaft is about 10 mm or less. In yet another embodiment, the length of the elongate shaft is about 5 mm or less.

In one embodiment, screw 103 is inserted into a receptacle in depression 125. It is desirable to have a threaded receptacle such that the screw is capable of being fixed to the plate 101. The screw 103 also passes over plate 107, and prevents it from vertically exiting depression 125. The placement of the screw receptacle is preferably chosen such that it is engageable with the ramped surface 305 of plate 107 when the plate is in its relaxed state, with its arm 301 extended.

Preferably, two screws 501 are inserted into openings 111 and 113. As the screws 501 are tightened, they will begin to lag the plate 101 to the bone. When the screw head 503 interferes with plate 107, it forces it to move towards the center of the plate 101. As the screws 501 are advanced further, the plate 107 forces its way back into its relaxed state. This causes the spherical curvatures 307-309 to form a complete spherical curvature around the screw head 503. When plate 107 is in its relaxed state, it prevents screw 501 from backing out. It may be desirable to tighten screw 103, such that plate 107 remains fixed in its relaxed state. In this manner, the screw 501 is prevented from backing out.

Screws 501 may be screwed into bony tissue at any desired angle. In other words, screw 501 does not have to be inserted perpendicular to the plate 101. The spherical properties of the head of the screw 503 and the spherical curvature of the openings 111-117 are preferably sufficient to prevent the screw from backing out. Thus, the largest diameter of the head of the screw is larger than the diameter of the narrowest portion of the opening in the top our outer side of the plate through which the screw head is placed. The interference difference between the fastener head diameter and the outer narrow opening may be describe in different ways depending on the size of the plate, openings, and fastener heads being used. For example the interference difference between the fastener head and the narrowest opening may be about 0.01 mm or greater, about 0.03 mm or greater, or about 0.10 or greater, or even about 0.20 mm or greater. Preferably, however, in each instance the interference is less than about 2 mm.

Alternatively, the interference between the fastener head and the narrow outer opening may be described relative to the outer diameter of the fastener head itself. For example, the interference may be about 0.5% or greater of the diameter of the fastener head, about 5% or greater of the diameter of the fastener head, or even about 10% or greater of the outer diameter of the fastener head. Preferably, however, in each instance the interference is less than about 40% of the outer diameter of the fastener head.

While openings 111-117 prevent the screws 501 from backing out, they do allow it to rotate freely within the spherical curvature. One advantage of allowing the screw 501 to rotate freely is that the bone fixation plate according to the present invention is able to accommodate for movements in the vertebrae or accommodate for compression of the bone grafts that are placed between vertebrae. Another advantage of allowing the screws to be inserted at any angle is that it allows relatively close spacing of the screws, without the risk of interference with one another.

Figure 6:
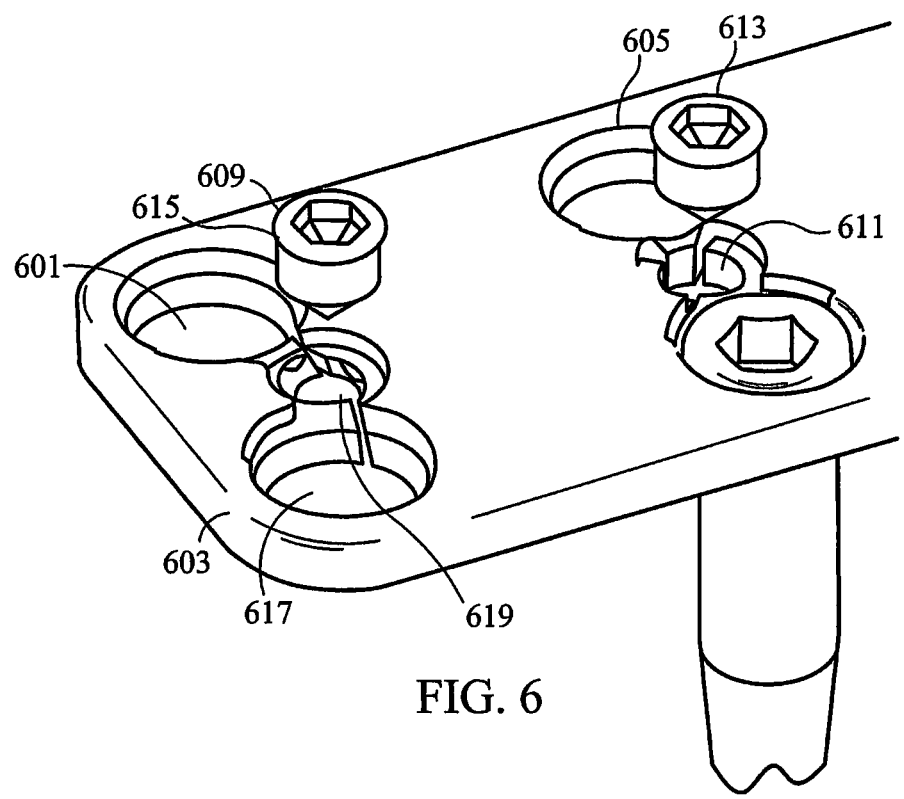
FIG. 6 is a diagram showing another embodiment of the bone fixation plate according to the present invention.

FIG. 6 shows another embodiment of the present invention. As shown in FIG. 6, an exemplary bone fixation plate according to the present invention comprises four openings 601-607. In one embodiment, openings 601-603 are connected to one vertebra, and openings 605-607 are connected to a second vertebra. Also included are two additional openings 609-611, which are located at a desired point between points 601-603 and 605-607, respectively. One advantage of the FIG. 6 embodiment is that a screw does not have to be inserted into opening 609 until after screws are inserted into openings 601-603. Thus, opening 609 serves as a window for a surgeon to view the vertebra, or space between adjacent vertebrae. This is often desirable to the surgeon.

Because all of the corresponding openings are similar, only openings 601-603 and 609 are described in detail. In one embodiment, openings 601 and 603 are spherical curvatures having the same properties discussed with respect to FIGS. 1-5. Thus, a complete description of the openings 601-603 is not repeated. The openings are substantially similar in size, shape, and diameter to the openings 111-117 described with respect to FIG. 1. There are some differences between the openings shown in FIG. 6 embodiment and the openings shown in the FIG. 1 embodiment which, are discussed below.

In one embodiment, the spherical curvature of openings 601-603 is substantially circular. The opening 601-603 comprises the majority of the circumference of the spherical curvature for the screw 613. This is in contrast to the spherical curvatures described with reference to FIGS. 1-5, which were formed by both the openings and the spring loaded plate 107. Therefore, the spherical curvature of each opening 601-603 houses substantially entire head of screw 613. In one embodiment, screw 613 is substantially similar to screw 501, discussed with reference to FIGS. 5A and 5B.

In one embodiment, the spherical curvature of the opening 601-603 comprises 90% or more of the total circumference of the curvature. In another embodiment, the spherical curvature of the opening 601-603 comprises 95% or more of the total circumference of the curvature. In yet another embodiment, the spherical curvature of the opening 601-603 comprises 99% or more of the total circumference of the curvature.

In one embodiment, opening 609 is selectively positioned between openings 601-603. Opening 609 preferably allows a screw 615 to pass, which increases the interference between the spherical curvature of the opening 601-603 and the head of the screw 613. As shown in FIG. 6, the placement of the openings 609-611 may be varied. In one embodiment, the opening may be positioned such that it positioned directly in between the openings or slightly higher than the openings. However, in another embodiment the opening 609-611 may be placed at a desired distance above the openings.

In order to use screw 615 to cause tighten the openings 601-603 around the head of screw 613, openings 601-603 comprise a fixed portion and a flexible portion 617. In one embodiment, flexible portion 617 is formed by a discontinuity that is formed in openings 601-603 and opening 609. When the flexible portion 617 of the opening is pushed against the screw 615, increased interference results. One advantage of the increased interference is that backout of the screw 615 is prevented.

The discontinuity 619 should be large enough that it allows flexure of portion 617 of the spherical curvature, while allowing the spherical curvature to maintain its structural integrity and provide a sufficient contact area for the head of the screw 613. In one embodiment, the discontinuity 619 shown in FIG. 6 comprises a small portion of the total circumference of the opening 601-603. The discontinuity 619 may be vertical, or it may be configured and dimensioned at a desired angle.

In one embodiment, the discontinuity 619 comprises about 5% or less of the total circumference of the curvature. In another embodiment, the discontinuity comprises about 3% of less of the total circumference of the curvature. In yet another embodiment, the discontinuity comprises about 1% or less of the total circumference of the curvature.

In the FIG. 6 embodiment, tangents to the curvature of opposing points along the spherical curvature intersect. This is in contrast to typical spherical curvatures that have been used for bone fixation plates, where the tangents to the curvature of opposing points do not intersect. One advantage of having the tangents to the curvature intersect is that the spherical curvature generates an interference area. As the head of the screw being screwed into place, a sufficient amount of force may be applied to force the head of the screw to contract slightly. As the screw is continues into the bone, the head of the screw is able to pass through the interference area. Once the head of the screw passes through the interference area it fits into the spherical curvature. It is desirable that forces that force the screw to backout are not strong enough to force the screw back through the interference area. This resistance of the interference area may be modified by changing its curvature.

Figure 7:
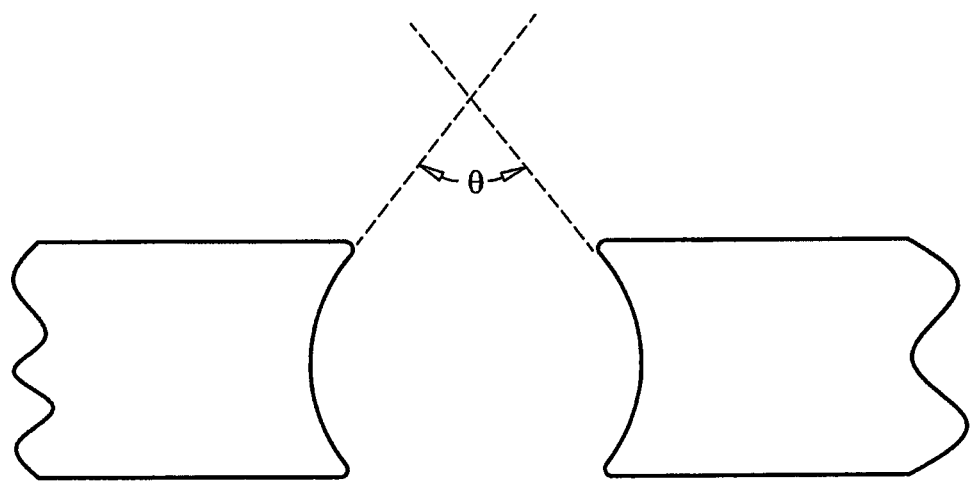
FIG. 7 is a diagram showing one embodiment of the spherical curvature according to the present invention.

In one embodiment, tangents to spherical curvature intersect to form an angle, as shown in FIG. 7. This angle is preferably between about 1 and about 10 degrees. In another embodiment, the angle between the tangents is between about 1 and about 5 degrees. In yet another embodiment, the angle between the tangents is between about 1 and about 3 degrees.

In one embodiment, opening 609 is substantially similar to openings 601-603. That is, it has a substantially spherical curvature. In other embodiments, however, opening 609 may not have a substantially spherical curvature. The curvature may be shaped to receive a screw 615 having a flat head. However, other types of screws may be used. In embodiments where screw 615 has threads, the receptacle may be configured to receive the threads in order to prevent screw 615 from backing out. To allow an instrument to grip the screw, a hexagonal depression may be configured on the head of the screw. However, in other embodiments it may be desirable to have a curved protrusion to aid in gripping the screw 615.

The diameter of opening 609 is preferably smaller than the diameter of openings 601-603. The diameter of opening 609 may be smaller than the diameter of openings 601-603 because the screw 615 that passes through the opening does not have to pass through bony tissue. In one embodiment, opening 609 and screw 615 function to further restrict openings 601-603 after the screw 613 has been inserted.

Screw 615 may be screwed into bony tissue at any desired angle. In other words, screw 615 does not have to be inserted perpendicular to the plate. The spherical properties of the head of the screw 615 and the spherical curvature of the openings 601-603 are preferably sufficient to prevent the screw from backing out. While openings 601-603 prevent screw 613 from backing out, they do allow it to rotate freely. One advantage of allowing the screw 613 to rotate freely is that the bone fixation plate according to the present invention is able to accommodate movements in the vertebrae or accommodate for compression of bone grafts that may be placed between vertebrae. Another advantage of allowing the screws to be inserted at any angle is that it allows relatively close spacing of the screws, without the risk of interference with one another.

Figure 8:
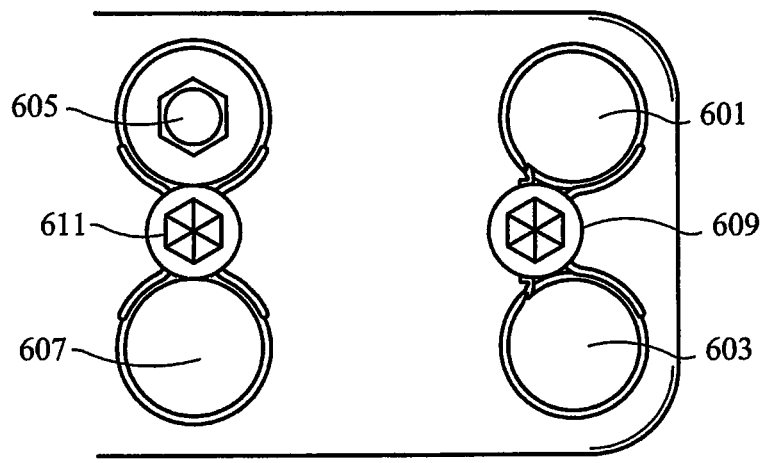
FIG. 8 is a diagram showing the forces exerted by the screws according to the embodiment shown in FIG. 6.

As described above, openings 609-611 may be placed in any desired position. In some embodiments, it may be desirable to position the opening 611 directly in line with openings 605-607. However, in other embodiments it may be desirable to place the opening 609 at a higher position than the openings 601-603. FIG. 8 is a diagram showing exemplary forces that may be exerted on the openings 601-607 when screws are inserted into openings 609 and 611.

As shown in FIG. 8, when the opening 609 is positioned at a higher position than openings 601-603, the screw exerts forces on parts 609-611 of the openings. Because the magnitude of interference between the openings 601-603 and the screw 613 is not as great, this embodiment may be preferable in applications where a significant amount of movement or shifting of the vertebrae is expected. The lower magnitude of interference allows the screws to shift to accommodate these movements. However, when the opening is positioned directly in line with openings 605-607, the screw exerts forces on a larger portion of the openings 605-607. Because of the increased magnitude of interference between the openings 605-607 and the screw 613, this embodiment may be desirable when it is preferable to have the plate held in place with more force.

Figure 9:
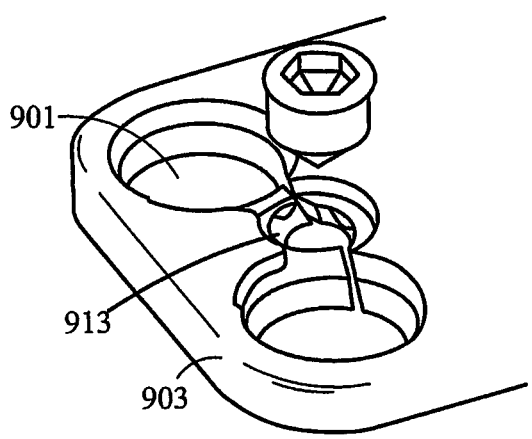
FIG. 9 is a diagram showing another embodiment of the bone fixation plate according to the present invention.
Figure 10A:
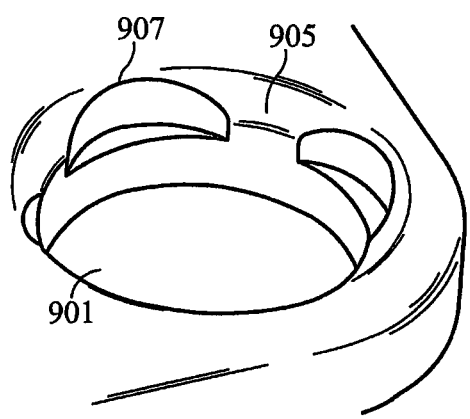
FIGS. 10A and 10B are illustrations of additional embodiments of bone fixation plates of the present invention.
Figure 10B:
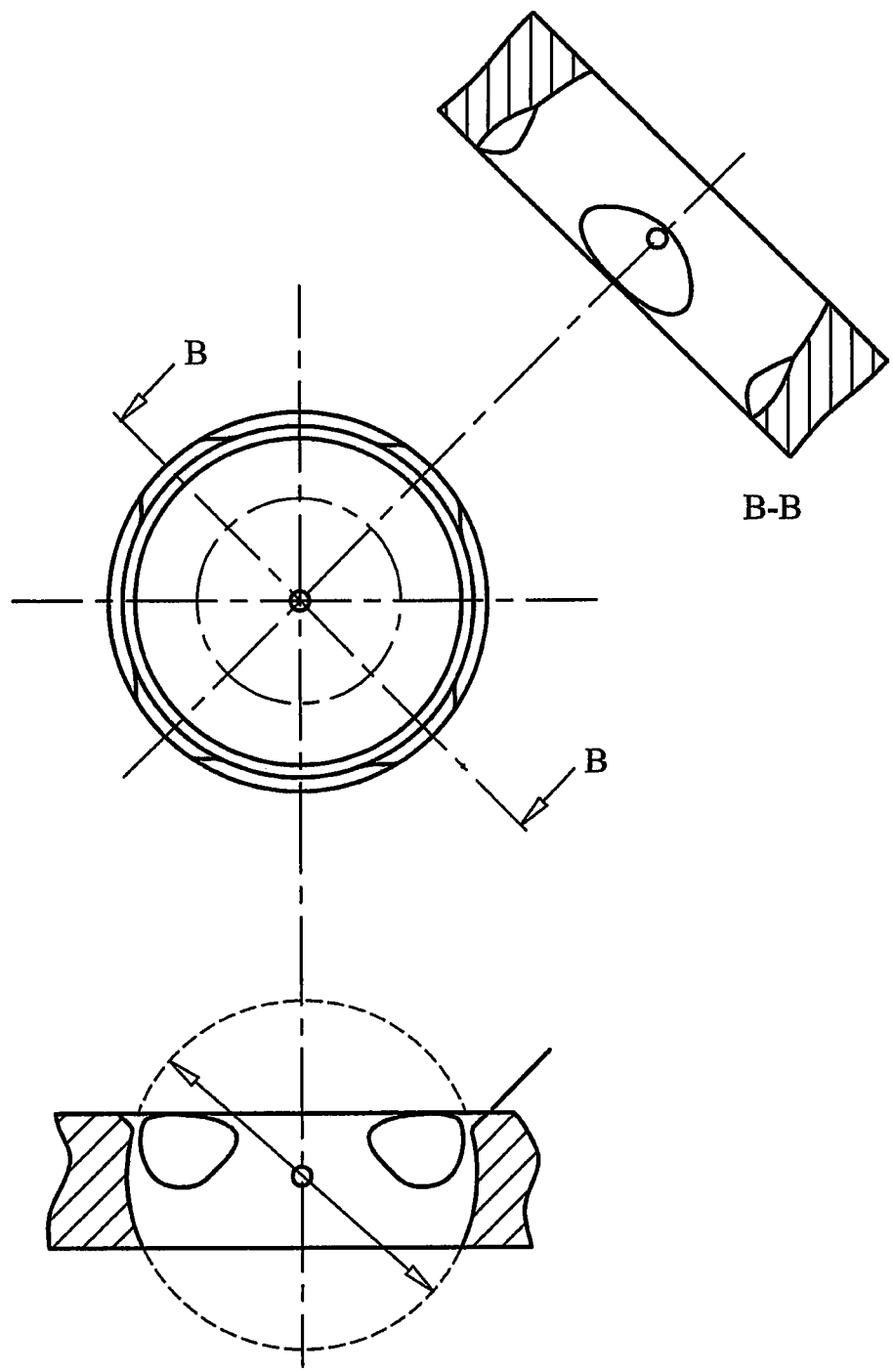

FIG. 9 is a diagram showing another embodiment of the present invention. In this embodiment, the present invention comprises at least two openings through which screws may pass. The screws used in this embodiment are similar to the screws described with respect to FIGS. 1-8, thus a discussion of them is not repeated. In some embodiments, a third opening may be selectively positioned between the at least two openings in order to prevent a screw from backing out of the openings. Though only one set of openings is shown in FIG. 9, a corresponding set of openings are also attached to an adjacent vertebra. Adjacent sets of openings are preferably connected by two elongate shafts.

As shown in FIG. 9, openings 901-903 comprise spherical curvatures, as described with reference to FIGS. 1-8. As described with reference to FIG. 7, tangents to the spherical curvature intersect to form an angle. The angles are similar to those discussed with reference to FIG. 7, and therefore are not repeated. In addition to the spherical curvature described with reference to FIG. 7, the FIG. 9 embodiment also includes alternating sections of engagement 905 and sections of relief 907. These sections of engagement 905 and relief 907 are preferably located along the top portion of the spherical curvatures, from which the screw is inserted. One advantage of having one or more sections of engagement and relief is that the openings 901-903 are able to accommodate micromotion of the screw, or in some cases, of the entire plate.

In one embodiment, the openings 901-903 comprise a single relief section 907. This provides the advantage of allowing a screw to adjust due to micromotion, while preventing the screw from backing out. In this embodiment, the remainder of the openings 901-903 is a section of engagement. The section of engagement preferably resists the motion of the screw.

In another embodiment, more than one section of relief 907 may be included. More than one relief section 907 may be desirable in embodiments where micromotion may be prevalent. The sections of relief 907 allow the angle of the screws to vary while preventing it from backing out. However, it is undesirable to include too many sections of relief 907. It is desirable to have more sections of engagement 905 than sections of relief 907 because too many sections of relief will result in the magnitude of the interference point being reduced at different angles. Thus, in a preferred embodiment, the openings 901 and 903 include more sections of engagement 905 than sections of relief 907.

In one embodiment, the number of relief sections 907 included in the openings is two or greater. In another embodiment, the number of relief sections that are included in the openings is four or greater. In yet another embodiment, the number of relief sections that are included in the openings is six or greater.

In some embodiments, the portions of the opening that are relief sections 907 and the portion of the openings that are engagement sections 905 may be expressed as a percentage of the total circumference of the openings 901-903. Preferably, the sections of relief comprise about 50% or less of the circumference of the openings. More preferably, the sections of relief comprise about 40% or less, and most preferably the sections of relief comprise about 30% or less of the circumference of the openings.

In one embodiment, a third opening 913 may be placed between openings 901-903. A set screw may be placed in opening 913 in increase the interference of the openings 901-903 against the head of the screw. In order to allow the screw to increase the interference between the openings 901-903 and the screw, a wedge shaped depression may be configured and dimensioned in the plate. The FIG. 9 embodiment provides the advantage of minimizing the profile of the bone fixation plate while increasing its ability to accommodate for micromotion.

In this embodiment, as a screw is tightened, it will begin to lag the plate to the bone. When the screw head interferes with the spherical curvature at an interference point, a small amount of resistance is generated. The interference, and resulting resistance, are caused by the angle of intersection of the tangents to the spherical curvature. As described above, the spherical curvature has tangents that intersect. The interference forces are easily overcome by the screw head. When the screw advances further, it snaps into the spherical curvature and is allowed to move freely. The forces which cause the screw to back out from the plate are preferably not strong enough to pass the screw head back past the interference section. To further assure that the screw head does not pass back past the interference section, the set screw described above may be employed.

Figure 11:
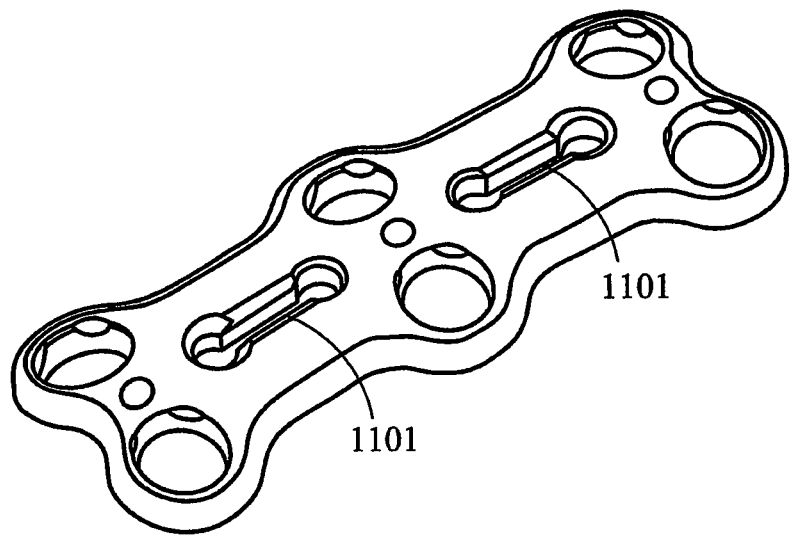
FIG. 11 is a diagram showing a one embodiment of the bone fixation plate according to the present invention.
Figure 12:
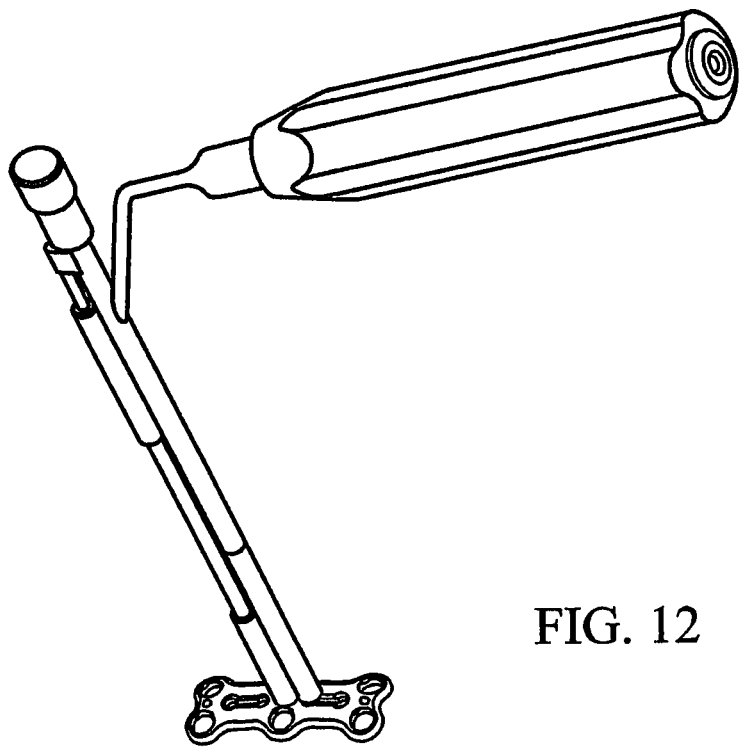
FIG. 12 is a diagram showing a drill guide in communication with a bone fixation plate of the present invention.
Figure 16:
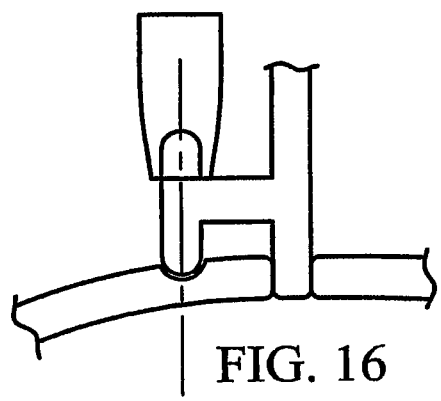
FIG. 16 is an illustration of one embodiment of a drill guide capable of rotating about an axis of a receptacle or depression formed in the plate.

Referring now to FIGS. 11-14, the plate of the present invention may be configured to aid in the insertion of bone screws. For example, FIG. 11 illustrates that the plate may have one or more openings 1101 that are capable of securely receiving a drill guide. For example, the openings may be configured with threads that engage with a threaded tip of the drill guide. In addition, the plate may also have one or more recesses, pivot points, depth stops, or areas of removed material in the top surface of the plate that help align the drill guide opening over the holes of the plate. The drill guide may have a rotating barrel that rotates along an axis that extends through the recess of the plate. In one embodiment, a portion of the drill guide can be aligned with and contact the recess while providing a base on which the barrel can rotate. Alternatively, as shown in FIG. 16, a portion of the barrel itself may reside in the recess of the plate upon which the drill guide may be rotatably disposed.

Figure 13:
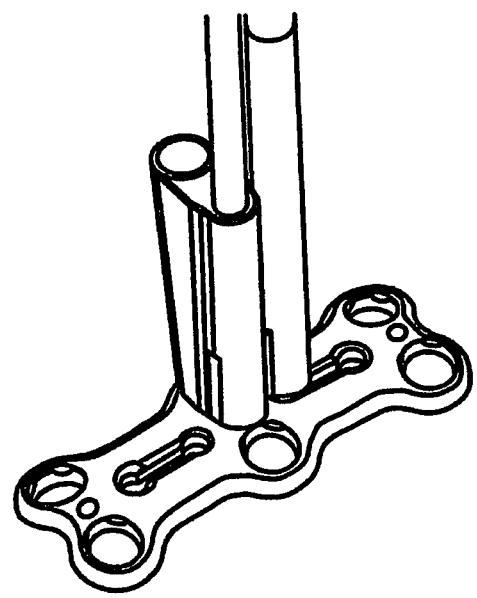
FIG. 13 is a magnified view of a drill guide in communication with a bone fixation plate of the present invention.
Figure 14:
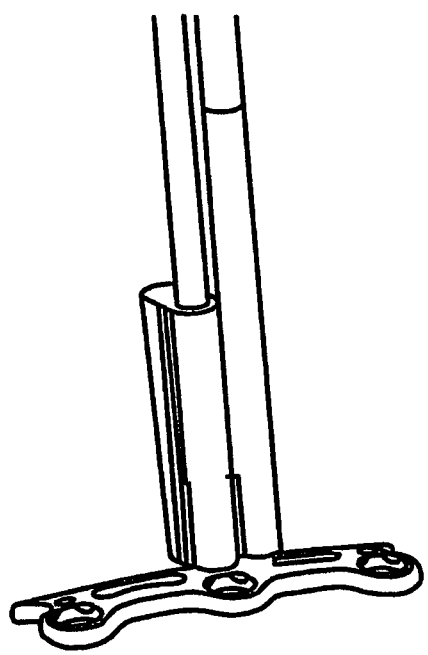
FIG. 14 is a side view of a drill guide in communication with a bone fixation plate of the present invention.

As shown in FIG. 13, the barrel may have a drill bore extending through its length. When the drill guide is properly aligned with the recess and opening, the barrel may be rotated to a first position such that the drill bore is aligned over a hole in the plate where a bone fastener will be placed. Preferably, the bore is configured so that its axis passes through the spherical opening in the plate. The portion of bone beneath the plate may then either be prepared for receiving a fastener by drilling a pilot hole in the bone, or alternatively a fastener may be placed directly into bone. To further ensure that the fastener is inserted at a proper angle, it may be inserted through the bore.

Once a first fastener has been inserted into a first hole of the plate, the barrel may be rotated such that it is aligned over a second hole in the plate, thereby allowing a second fastener to be inserted without having to reposition the entire drill guide. As shown in FIGS. 11-14, a plurality of guide holes and recesses may be provided in the plate. In one embodiment, one recess and guide hole may be used to insert fasteners into two bone screw holes.

As discussed above, once a fastener head has passed the interference area it may freely swivel or rotate to accommodate different angles or to allow for reabsorption of graft material over time. As graft material or bone is reabsorbed by the body, loading previously borne by the bone may be transferred instead to the plate. Thus, in may be preferable in some circumstances to have one or more fastener, more preferably two or more fasteners remain substantially free to swivel or rotate to account for dimensional changes in the bone that may occur after insertion of the plate.

In some cases, however, it may be desirable to rigidly fix the angle of the fastener relative to the plate once it is deployed. While some devices have been developed in the past to help resist or prevent micromovement of a plate relative to a fastener or to the bone that the plate contacts, past designs have either lacked the ability to be inserted at varying angles or have required complex designs or additional components in order to achieve multi-angel variability.

One example is described in U.S. Pat. No. 4,484,570, which is incorporated herein in its entirety. In particular, this reference discusses that reabsorption of the bone may take place at a portion of the contact surface between the bone and the plate. Over time, this reabsorption can cause open gaps to be formed, which may eventually become large enough that varying loads acting on the bone can cause undesirable micromovement between the plate, bone, and fasteners. This reference addresses this issue by describing a fastener having a head configured with a generally conical outer surface and having one or more slots. The fastener head further has a clearance hole or receptacle in which an expanding set screw may be inserted to splay or direct portions of the slotted head radially outwards. The interior surface of the fastener head is also generally conical and corresponds to a conical outer surface of the set screw. Thus, as the set screw is driven further into the clearance hole or receptacle, the interaction between the two conical surfaces applies progressively greater amounts of locking force. As mentioned above, one disadvantage to the locking fastener system described in the '570 patent is that it is not capable of permitting adjustability of the fastener with respect to the plate.

Another example is found in U.S. Pat. No. 6,235,033, which also is incorporated herein in its entirety. In particular, the '033 patent purports to achieve multi-angle variability of a plate design based substantially upon the addition of a c-ring to the design described in the '570 patent. In particular, the '033 patent likewise teaches to use a fastener having a slotted head with a generally conical outer surface. The conical surface of the fastener can be connected to a c-ring that resides in the opening of the plate through which the fastener is inserted. The outer surface of the c-ring slidingly engages with the spherical surface of the hole in the plate to provide variation in the angle of the fastener. When desired, an expansion screw may be deployed in a receptacle formed in the fastener head so that the outer surface of the fastener head apply outward pressure against the c-ring. Eventually, the c-ring expands sufficiently to apply pressure against the opening in the plate that locks the fastener relative to the plate. One disadvantage to this multi-angle locking system, however, is that it requires that the plate be assembled with a c-ring in each opening or hole through which a fastener will be placed.

While any of the various methods and techniques described in these references for having the fastener head capable of applying an outward force may be used, the present invention also relates to an improved way to achieve multi-angle variability while preserving simplicity of design. Rather than using a complex, multi-piece plate construction or sacrificing the ability of the fastener to have variable angles relative to the plate, the present invention contemplates forming the outer surface of a slotted fastener head to have a curved or spherical shape corresponding generally to the curvature of a portion of the plate holes in which the fastener will be placed. Thus, the fastener may be inserted into a plate hole at a variety of angles and be selectively locked in position without the use of a c-ring, bushing, or the like to aid in providing multi-angle variability. Once the fastener is in its desired position, a set screw may be inserted into a receptacle in the fastener head to rigidly hold the fastener in a fixed position relative to the plate.

The outer surface of the curved fastener head may be textured to provide increased locking forces. For example, a portion of the outer surface of the fastener head may be configured with circular grooves that help hold the fastener in place as the slotted head is expanded outward against the inner surface of the plate hole. Likewise, the outer surface of the fastener may be roughened to provide increased resistance to slippage between the fastener head and the plate when in a rigid position.

Figure 15B:
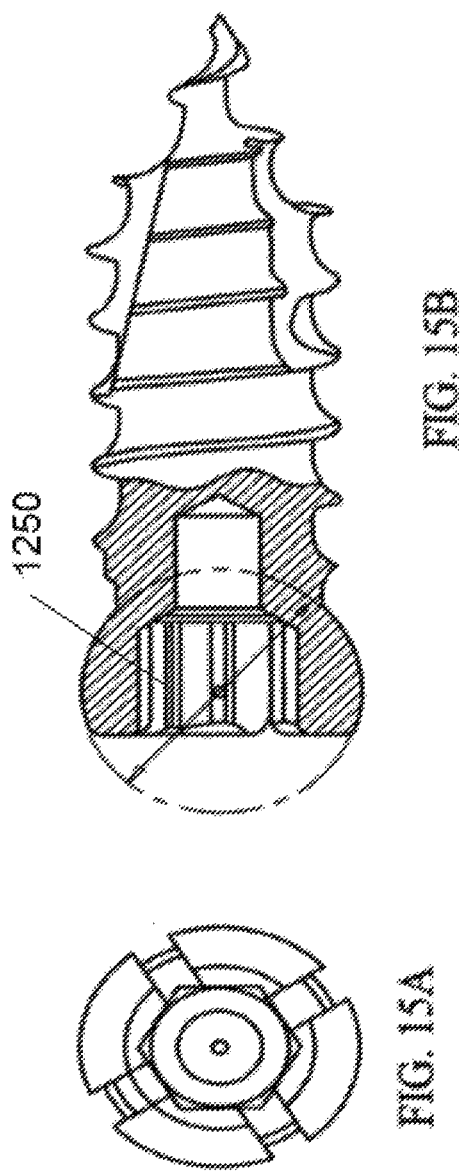
FIGS. 15A-C are diagrams showing an exemplary embodiment of a rigid bone screw according to the present invention.
Figure 15C:
Figure 15A:
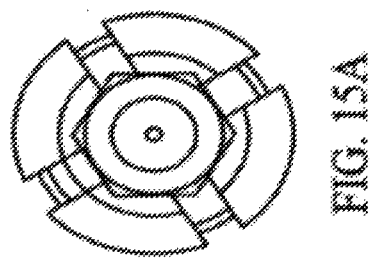

FIGS. 15 A-C illustrate one example of a fastener of the present invention that is capable of selectively providing the ability to swivel or move and to hold a fixed position. In particular, the fastener head has an outer surface that is generally spherical in shape, thereby allowing it to rotate or swivel once past the interference area. The fastener head also has a plurality of slots or cuts in the head that permit the head to expand or compress. The fastener head also may have an interior space that is capable of securely receiving a second fastener 1250, such as a set screw, a cam, or the like. As the second fastener is inserted into this interior space, its causes the diameter of the first fastener head to increase and press against the inner wall of the bone screw opening in the plate, thereby locking it in place. As stated above, the outer surface of the first fastener head may be textured to further increase the ability to rigidly hold the fastener in place.

The inner space of the first fastener and outer shape of the second fastener may have different configurations to create and apply a locking force. For example, in one embodiment the set screw, interior space, or both may have a generally conical shape that progressively applies greater outward forces as the set screw or second fastener is inserted. Likewise, the interior space, second fastener head, or both may be generally cylindrical with the diameter of the second fastener being greater than the inner diameter of the interior space.

Thus, in accordance with the present invention, the bone fixation plates and components described with reference to FIGS. 1-15 may be secured to vertebrae and other bony material in a manner that prevents the screws from working loose when subject to vibration. Furthermore, the embodiments described above prevent the backing out of screws while minimizing the profile of the bone fixation plate. Retaining features, provided near each opening through which a screw may pass, is moveable between relaxed and flexed positions. Another advantage of the present invention is that screws that fasten the plate to the bony tissue may be oriented at a variety of non-perpendicular angles with respect to the plate, which allows a relatively close spacing of fasteners without the risk of fasteners interfering with one another.

Although the present invention has been described with respect to several embodiments, it will be understood by those skilled in the art that the present invention is capable of alternate embodiments within the spirit of the appended claims. For instance, while the embodiments described herein refer to a plate useful for the cervical region of the spine, skilled artisans would understand that the plate design described herein may also be used in other regions of the spine or even for fixation of other bones in other parts of the body. Thus, the invention is not limited only to treating the cervical spine.

What is claimed is:

1. A fastener system for mounting an implant to bone comprising:
   an elongate fastener having a longitudinal axis, a proximal end, and a distal end;
   a shaft portion including a threaded portion disposed on the distal end of the fastener, wherein said threaded portion is capable of screwing into bone;
   a fastener head disposed on the proximal end of the fastener, wherein the fastener head comprises:
      a partially spherical outer surface;
      an interior surface defining a receptacle for receiving a locking fastener, wherein the interior surface is non-threaded; and
      at least one slit extending between the outer surface and interior surface of the fastener head to permit outward expansion of the fastener head, the at least one slit extending exclusively along a length of the fastener head without entering the shaft portion;
   a locking fastener capable of being received in the receptacle of the fastener head,
   wherein the locking fastener has a different configuration than the receptacle to create and apply a locking force; and
   a plate having at least one aperture including an interference area integrally formed therein configured to prevent the elongate fastener from backing out of the interference area,
   wherein the at least one aperture has a spherical curvature extending at least partially through the thickness of the plate, wherein insertion of the fastener head interferes with the interference area, and wherein the fastener head is capable of engaging with and passing the interference area to communicate with the spherical curvature.

2. The fastener system of claim 1, wherein the fastener head comprises two or more slits extending between the outer surface and interior surface of the fastener head to permit outward expansion of the fastener head.

3. The fastener system of claim 1, wherein the fastener head comprises four or more slits extending between the outer surface and interior surface of the fastener head to permit outward expansion of the fastener head.

4. The fastener system of claim 1, wherein the locking fastener is a cam.

5. The fastener system of claim 1, wherein the interior surface defining the receptacle and an outer surface of the locking fastener are of different configurations to create a locking force.

6. The fastener system of claim 1, wherein the interior surface defining the receptacle and an outer surface of the locking fastener are generally cylindrical with the diameter of the locking fastener being greater than the diameter of the interior surface.

7. The fastener system of claim 1, wherein the interference area includes alternating sections of engagement and sections of relief.

8. A fastener system for mounting an implant to bone comprising:
- an elongate fastener having a longitudinal axis, a proximal end, and a distal end;
- a fastener head disposed on the proximal end of the fastener, wherein the fastener head comprises at least one slit located on the fastener head to permit outward expansion of the fastener head, the at least one slit extending exclusively along a length of the fastener head without entering a shaft portion, wherein the fastener head further comprises an interior surface defining a receptacle for receiving a locking fastener, wherein the interior surface is non-threaded;
- a locking fastener capable of being received in the receptacle formed in the fastener head,
- wherein the locking fastener has a different configuration than the receptacle to create and apply a locking force; and
- a plate having at least one aperture including an interference area integrally formed therein configured to prevent the elongate fastener from backing out of the interference area,
- wherein the at least one aperture has a spherical curvature extending at least partially through the thickness of the plate, wherein insertion of the fastener head interferes with the plate at the interference area, and wherein the fastener head is capable of engaging with and passing the interference area to communicate with the spherical curvature.

9. The fastener system of claim 8, wherein the fastener comprises a partially spherical outer surface.

10. The fastener system of claim 8, wherein the locking fastener comprises a cam.

11. The fastener system of claim 8, wherein the fastener head comprises two or more slits extending between an outer surface and interior surface of the fastener head.

12. The fastener system of claim 8, wherein the fastener head comprises four or more slits extending between an outer surface and interior surface of the fastener head.

13. The fastener system of claim 8, wherein the interior surface defining the receptacle in the fastener head and an outer surface of the locking fastener are of different configurations to create a locking force.

14. A fastener system for mounting an implant to bone comprising:
- an elongate fastener having a longitudinal axis, a proximal end, and a distal end;
- a fastener head disposed on the proximal end of the fastener, wherein the fastener head comprises at least one slit located on the fastener head to permit outward expansion of the fastener head, the at least one slit extending exclusively along a length of the fastener head without entering a shaft portion, wherein the fastener head further comprises an interior surface defining a receptacle, wherein the interior surface is non-threaded;
- a locking fastener capable of being received in the receptacle formed in the fastener head, wherein the locking fastener has a different configuration than the receptacle to create and apply a locking force, and
- a plate having at least one aperture including an interference area integrally formed therein configured to prevent the elongate fastener from backing out of the interference area,
- wherein the elongate fastener is configured to interfere with the interference area, and
- wherein the interference area includes a plurality of relief areas and a plurality of engagement areas,
- wherein the interior surface defining the receptacle in the fastener head and an outer surface of the locking fastener are generally cylindrical with the diameter of the locking fastener being greater than the diameter of the interior surface.

15. The fastener system of claim 14, wherein the locking fastener comprises a cam.

* * * * *